United States Patent
Taheri (12) 
(10) Patent No.: US 6,659,995 B1
(45) Date of Patent: Dec. 9, 2003

(54) AUTOLOGOUS MYOCYTE MICRO GRANUAL RETRIEVAL AND IMPLANTATION (AMMGRI)

(76) Inventor: Syde A. Taheri, 1275 Delaware Ave., Buffalo, NY (US) 14209

( * ) Notice: Subject to any disclaimer, the term of this patent is extended or adjusted under 35 U.S.C. 154(b) by 0 days.

(21) Appl. No.: 09/715,913

(22) Filed: Nov. 17, 2000

(51) Int. Cl.[7] ............................................... A61M 31/00
(52) U.S. Cl. ........................ 604/500; 604/507; 604/522; 424/93.1
(58) Field of Search ................................. 604/507, 511, 604/500, 502, 506, 508, 518, 522; 424/93.1; 128/898

(56) References Cited

U.S. PATENT DOCUMENTS

| | | | | |
|---|---|---|---|---|
| 5,902,279 A | * | 5/1999 | Powles et al. | 600/578 |
| 6,110,459 A | * | 8/2000 | Mickle et al. | 424/85.1 |
| 6,151,525 A | * | 11/2000 | Soykan et al. | 607/3 |
| 6,395,016 B1 | * | 5/2002 | Oron et al. | 128/898 |

OTHER PUBLICATIONS

Suzuki, et al., Circulation. 2000; 102 [suppl III]: III–359–III–364.*

* cited by examiner

*Primary Examiner*—Brian L. Casler
*Assistant Examiner*—Matthew DeSanto (74) *Attorney, Agent, or Firm*—Walter W. Duft (57) ABSTRACT

In a method for autologous myocardial implantation treatment, a donor area of a patient containing healthy skeletal muscle is located. Myocyte micro granules are retrieved from the donor area using a retrieval device and either directly implanted into an implantation area of the patient's myocardium, or they are transferred to an implantation device and then implanted. No intervening cell culturing is performed between myocyte micro granule retrieval and implantation. A retrieval device that may be used to retrieve the myocyte micro granules from the donor area includes one or more extraction probes each having a distal tip adapted to be inserted into the skeletal muscle of the donor area. The retrieval device further includes a retrieval system that causes each distal tip to withdraw a myocyte micro granule upon removal thereof from the donor area. An implantation device that may be used to implant the myocyte micro granules includes a tubular body, an injection tip on the body that is adapted to enter the damaged area and deliver the micro granules, and a plunger within the body for pushing the micro granules through the injection tip. In one configuration of the implantation device that is especially adapted for implantation according to an epicardial approach, the device includes a handle extending laterally from the body for grasping by a medical practitioner when the injection tip is placed in the beating myocardium. In another configuration of the implantation device that is especially adapted for implantation according to a transfemoral approach, the device includes a retractable screen system for blocking myocyte micro granules from leaving the myocardium during implantation.

19 Claims, 9 Drawing Sheets

AUTOLOGOUS MYOCYTE MICRO GRANUAL RETRIEVAL AND IMPLANTATION (AMMGRI)

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention relates to cardio myopathy and the treatment thereof.

2. Description of the Prior Art

By way of background, cardio myopathy, as caused for example by myocardial infarction, is a common disorder. Twenty thousand new cases are reported yearly in the United States and 25–50% of such cases will result in death after three years. The problem is that damaged adult heart muscle does not regenerate and myocardial functionality cannot be restored using the body's natural healing mechanisms. The myocardium tends to dilate and areas of the ventricular walls may become hypokinetic, or even akinetic, such that congestive heart failure often develops in affected individuals.

Previous medical techniques have not substantially reduced the morbidity or mortality of this condition. Past efforts in this area include removing autologous muscle cells, stem cells, etc., and culturing them to generate the large number of implantation cells necessary for myocardial repair. The cultured cells are then implanted via injection or the like into the myocardium, where they have an opportunity to regenerate new heart muscle. However, cell culturing requires sophisticated equipment, is expensive, and involves a delay of several weeks as the cell culture grows. This makes it impossible, for example, to use implantation treatment as an adjunct to emergency coronary bypass surgery. Instead, a separate implantation procedure is required that must await maturation of the patient's autologous cell culture.

Accordingly, a need exists for an improved treatment to repair, and restore functionality to, a damaged myocardium resulting from myocardial infraction or the like. What is required is an autologous myocardial implantation method that overcomes the foregoing disadvantages of conventional implantation procedures. What is especially needed is an implantation method that allows immediate use of harvested autologous implantation tissue for implantation during emergency coronary bypass operations and other procedures where time is of the essence.

SUMMARY OF THE INVENTION

The foregoing problems are solved and an advance in the art is obtained by a novel method and apparatus for autologous myocardial implantation treatment. According to the method, a donor area of a patient containing healthy skeletal muscle is located. Using a suitable retrieval device, the practitioner retrieves myocyte micro granules from the donor area and either transfers them to a suitable implantation device or leaves them in the retrieval device if that device is also adapted for micro granule implantation. After locating an implantation area of the patient's myocardium that contains damaged myocardial tissue, the myocyte micro granules are implanted into the implantation area. No intervening cell culturing is performed between myocyte micro granule retrieval and implantation.

A myocyte micro granule retrieval device is provided for retrieving the myocyte micro granules from a donor area. This device includes one or more extraction probes, each having a distal tip that can be advanced into the skeletal muscle of the donor area, and a retrieval system for causing the distal tips to each withdraw a myocyte micro granule upon removal thereof from the donor area.

A myocyte micro granule implantation device can also be provided for implanting the myocyte micro granules in a damaged area of a patient's myocardium. This device includes a tubular body, an injection tip on the body that is adapted to enter the damaged area and deliver the myocyte micro granules, and a plunger within the body for pushing myocyte micro granules through the injection tip. In one configuration of the implantation device especially adapted for implantation according to an epicardial approach, the device includes a handle extending laterally from the body for grasping by a medical practitioner when the injection tip is inserted in the beating myocardium.

In another configuration of the implantation device especially adapted for implantation according to a transfemoral approach, the device includes a retractable screen system for blocking myocyte micro granules from leaving the myocardium during implantation.

BRIEF DESCRIPTION OF THE DRAWING

The foregoing and other features and advantages of the invention will be apparent from the following more particular description of preferred embodiments of the invention, as illustrated in the accompanying Drawing, in which.

DETAILED DESCRIPTION OF THE PREFERRED EMBODIMENT

1. AMMGRI PROCEDURE

The procedure of the invention may be referred to as Autologous Micro Granule Myocyte Retrieval and Implantation ("AMMGRI"). In its preferred embodiment, this procedure begins with surgical exposure of (or insertion of a laproscopic instrument in proximity to) a donor area of a patient containing skeletal muscle. This could be abdominal wall muscle, leg muscle, rectus muscle, or striated muscle from any other suitable area of the patient's body. A retrieval device (an example of which is described below) is used to obtain myocyte micro granules from the donor area. The micro granules are very small muscle segments that have a maximum dimension on the order of about 1 millimeter or less. Notwithstanding their small size, each micro granule will preferably contain as many as 1–2 million myocyte cells, although micro granules containing as few as about 100,000 myocyte cells or less may suffice in some cases.

If desired, the myocyte micro granule donor area can be pretreated with an angiogenesis-promoting material by injection directly into the donor area. Alternatively, the angiogenesis-promoting material could be introduced into a blood vessel that supplies blood to the donor area. Such materials may include 1) growth factors, 2) transvected genes, 4) enzymes, 5) cytokines, or 6) any of various medications adapted to promote healing.

Following removal from the donor area, the myocyte micro granules could be directly implanted in a myocardium, provided the retrieval device is also adapted for implantation. More preferably, however, the myocyte micro granules are deposited in a fluid carrier, such as a liquid medium (e.g., saline), and mixed therewith. Then, without cell culturing, the myocyte micro granules are transferred to either the original retrieval device (if it is adapted for implantation) or to a separate implantation device (examples of which are described below). Using a transfemoral or epicardial approach, the myocyte micro granules are implanted into the damaged area of the myocardial wall. Micro granule integration with existing myocardial tissue, along with associated angiogenesis, and will now occur via the body's natural healing mechanisms to repair the heart. Note that if a transfemoral approach is used, it may be desirable to block the aorta via a screen device to prevent loose micro granules that may spill out of the injection site from entering the aorta. An example of such a screening device is described below.

2. APPARATUS FOR PERFORMING AMMGRI

A. Myocyte Micro Granule Retrieval

Figure 1:
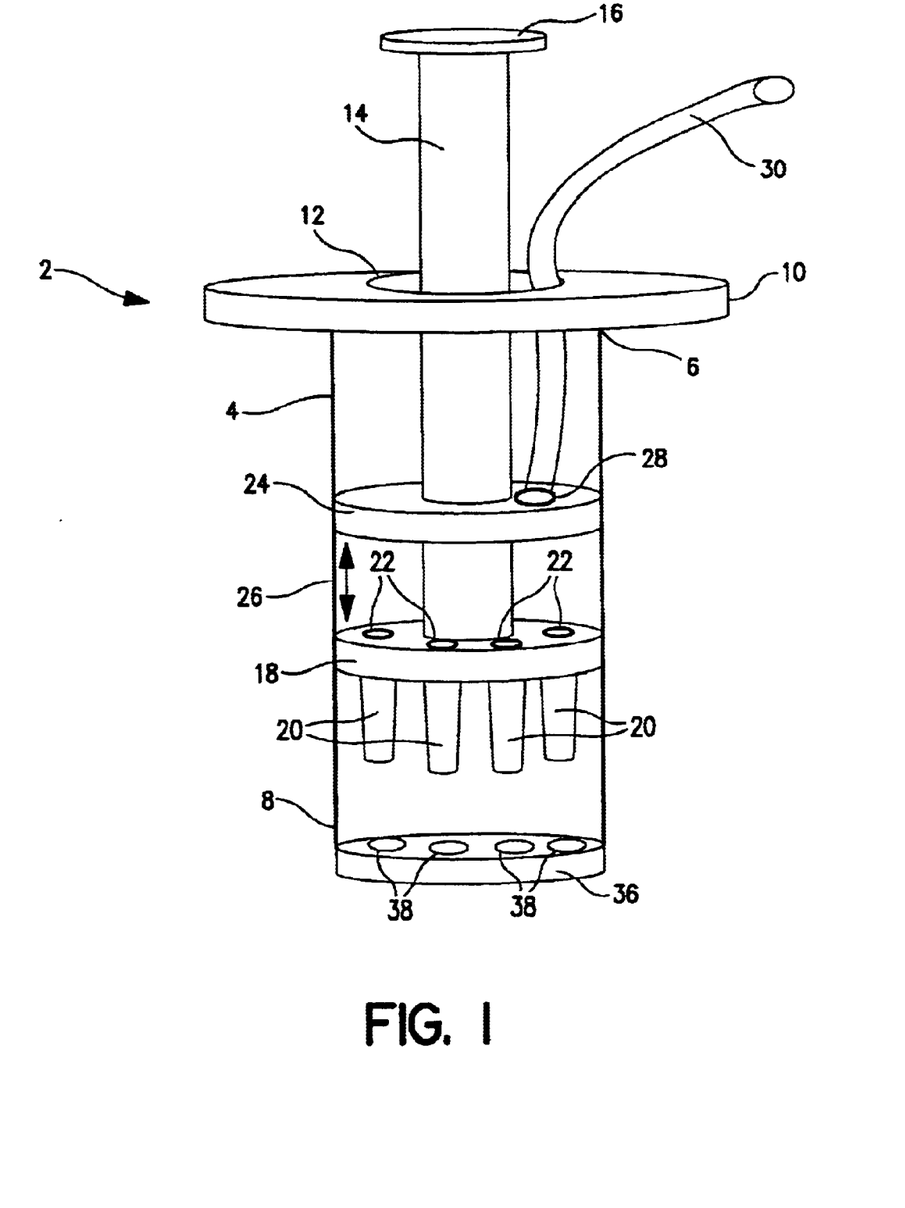
FIG. 1 is a perspective view of a myocyte micro granule retrieval device for use in practicing a portion of the myocyte micro granule retrieval and implantation method of the invention.

Turning now to the figures, wherein like reference numerals represent like elements in all of the several views, FIG. 1 illustrates a preferred myocyte micro granule retrieval device 2 that may be used for myocyte micro granule retrieval as described above. The retrieval device 2 recovers myocyte micro granules using a vacuum assist approach. To that end, the retrieval device 2 includes a substantially tubular body 4 having a proximal end 6 and a distal end 8. A flanged cover 10, which allows the retrieval device 2 to be manually grasped and held in place during myocyte micro granule removal, is secured at the proximal end 6. The cover 10 includes a central aperture 12 that slidably receives a plunger assembly 14. The plunger assembly 14 has a thumb support 16 at its proximal end 6, and a lower disk 18 mounted at its distal end 8. Note that all of the foregoing components can be made from any material that is suitable for medical use, such as surgical grade plastic.

Mounted to and extending downwardly from the lower disk 18 are a plurality of hollow myocyte micro granule extraction probes 20, preferably made from stainless steel or the like. Each extraction probe 20 has a central bore 22 extending therethrough, and these bores can be seen as being exposed at the upper side of the lower disk 18. As described below, each extraction probe 20 is adapted to retrieve a single myocyte micro granule.

Figure 2:
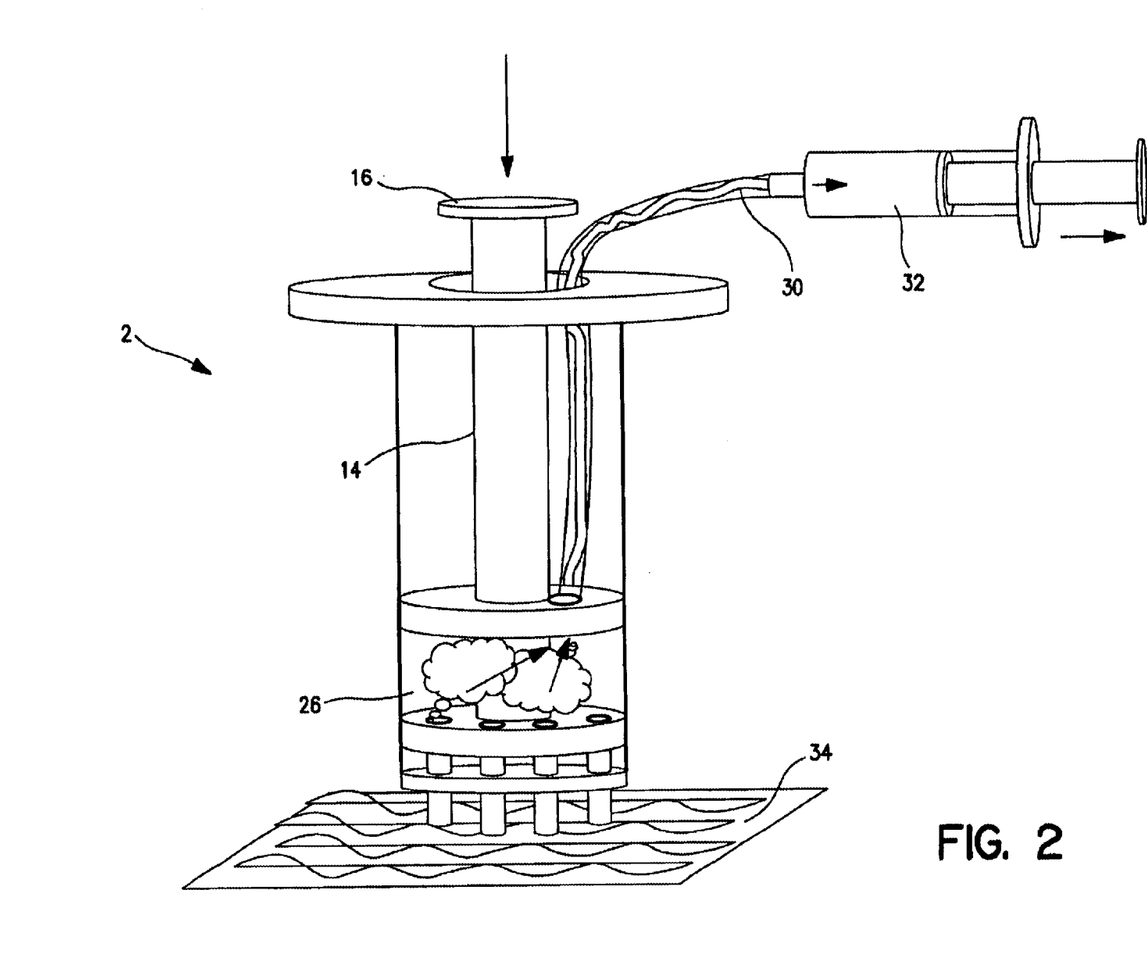
FIG. 2 is a perspective view of the myocyte micro granule retrieval device of FIG. 1, showing penetration of the retrieval device's myocyte micro granule extraction probes into a donor area and evacuation of the retrieval device's vacuum chamber to apply a suction force at the tips of the extraction probes.

Disposed in spaced relationship with the lower disk 18, and located at a medial portion of the plunger assembly 14, is an upper disk 24 made from surgical grade plastic or the like. In combination, the lower disk 18 and the upper disk 24 form a vacuum chamber 26. To that end, the outer circumferences of the disks 18 and 24 maintain a slidable (but snug) engagement with the inner wall of the tubular body 4. Although not shown, a ring seal member made of a resilient polymer or other suitable material may be mounted around the circumference of each of the disks 18 and 24 so as to provide an airtight vacuum seal between the disks and the tubular body inner wall. In order to apply a vacuum to the vacuum chamber 26, the upper disk 24 is provided with an air hole 28 to which a plastic tube 30 is attached. As shown in FIG. 2, the tube 30 is used as a passage through which air is withdrawn using a syringe 32 or other suitable vacuum device (such as a vacuum pump) to create a vacuum in the vacuum chamber 26.

FIG. 2 shows the retrieval device 2 placed against a donor area 34 of a patient. The plunger assembly 14 has been lowered by a medical practitioner applying thumb pressure to the thumb support 16, thereby forcing the extraction probes 20 into the patient's skeletal muscle. With the extraction probes 20 inserted in skeletal muscle, the syringe 32 attached to tubing 14 is used to draw air from inside the vacuum chamber 26, thereby applying a vacuum to the tips of the extraction probes 20. If desired, a removable plate 36, made from plastic or the like and with holes 38 coinciding in position with the extraction probes 20, can be mounted over the distal end 8 of the tubular body 4. The plate 36 helps position the retrieval device 2 on the donor area and assists in the presentation of skeletal muscle for removal by the extraction probes 20. In particular, the skeletal muscle will tend to bulge through the holes 38 and will be tensioned so as to make it easier for the extraction probes 20 to enter the muscle.

Figure 3A:
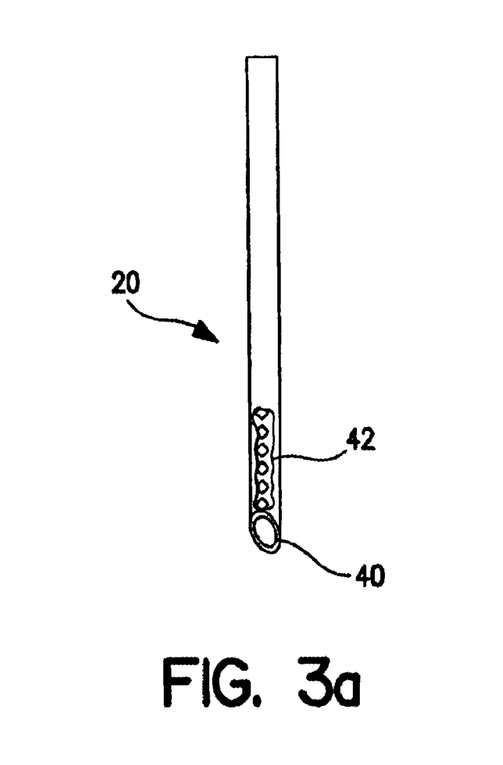
FIG. 3a is a detailed side elevation view showing an exemplary myocyte micro granule extraction probe for use in the retrieval device of FIG. 1.
Figure 3B:
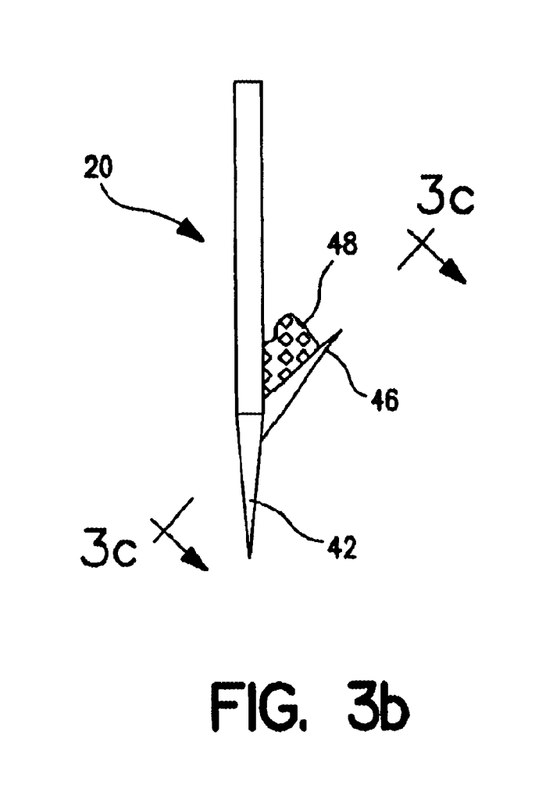
FIG. 3b is a detailed side elevation view showing an alternative myocyte micro granule extraction probe for use in the retrieval device of FIG. 1.
Figure 3C:
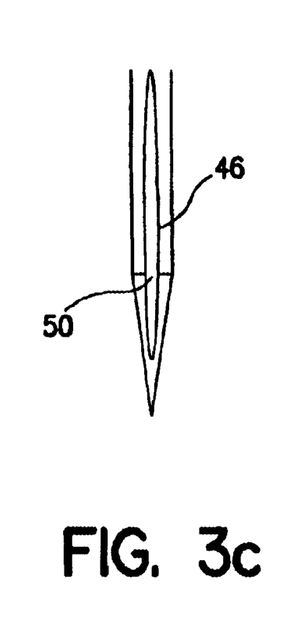
FIG. 3c is a cross-sectional view taken along line 3c—3c in FIG. 3b showing a barb on the myocyte micro granule extraction probe of FIG. 3b.
Figure 4:
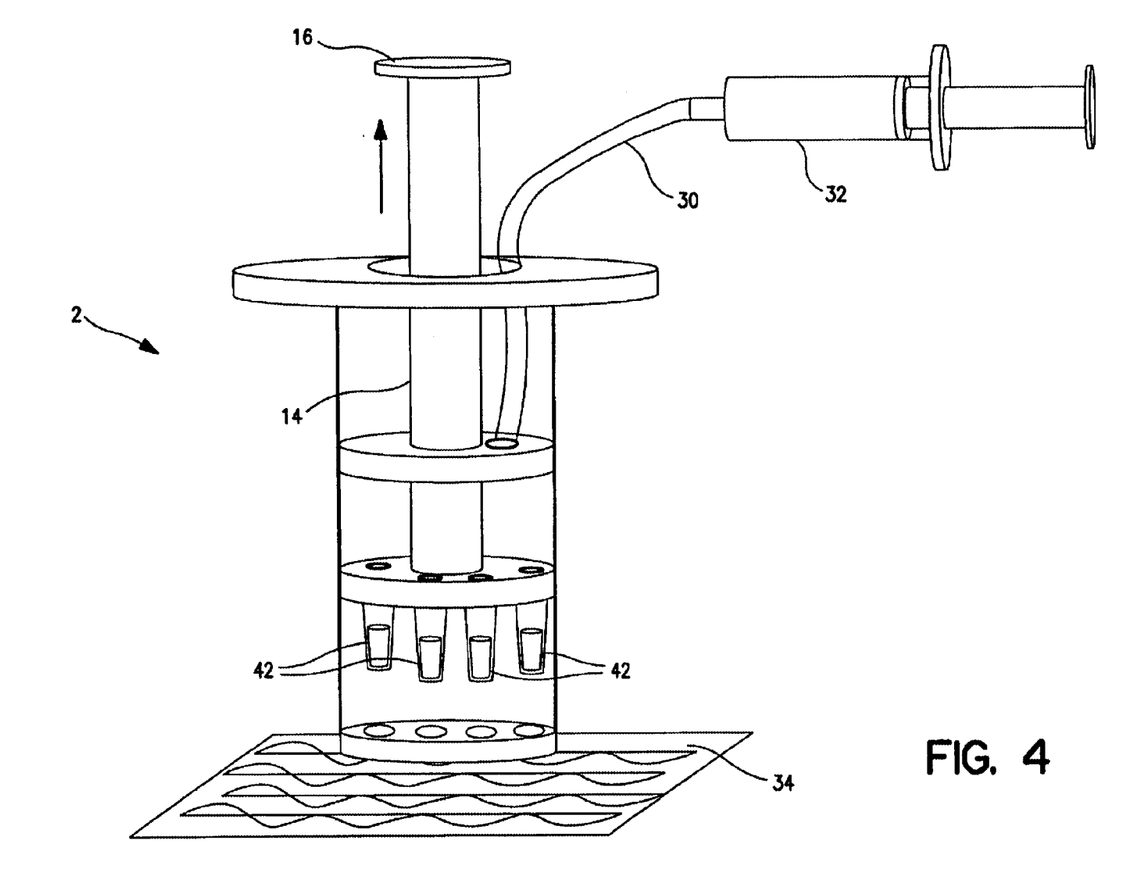
FIG. 4 is a perspective view of the myocyte micro granule retrieval device of FIG. 1, showing withdrawal of myocyte micro granules from a donor area.

Turning now to FIGS. 3a, 3b, and 3c, two design alternatives for the extraction probes 20 are shown in detail. FIG. 3a illustrates a design wherein the extraction probe 20 is configured as a straight hollow needle with a slanted open end 40. When the extraction probe 20 is introduced into the donor area, the open end 40 pierces the skeletal muscle and a short column or plug of skeletal muscle enters the central bore 22. After vacuum is applied to the vacuum chamber, as shown in FIG. 2, the extraction probes 20 can be withdrawn from the donor site by raising the plunger assembly 14. As this happens, the skeletal muscle within each extraction probe 22 will be pulled until it separates from the donor area, thus forming a myocyte micro granule 42, as shown in FIG. 4. Each extraction probe 20 thus retrieves on myocyte micro granule 42.

In FIG. 3b, the extraction probe 20 is configured as a straight, solid needle having a pointed closed end 44, and a pointed barb 46. Note that this configuration is intended for use without a vacuum being present in the vacuum chamber 26. Extraction probes according to this configuration could also be used in other myocyte micro granule retrieval devices having one or several of such extraction probes, all operating without vacuum. The barb 46 serves to recover a myocyte micro granule 48 by entering the donor area and then pulling out skeletal muscle that it encounters by cutting while exiting the donor area. To ensure that a sufficient quantity of skeletal muscle is removed, the barb 46 may be formed with a hollow channel or trough 50, as shown in FIG. 3c, that provides a receptacle for the myocyte micro granule, thereby allowing it to be excised without a vacuum.

FIG. 4 illustrates the retrieval device 2 with the extraction probes 20 withdrawn from the donor area 34. As can be seen, each extraction probe 20 contains a myocyte micro granule. If the extraction probes 20 are configured according to FIG. 3a, each will carry a vacuum-recovered micro granule 42, as shown in FIG. 4. If the extraction probes are configured according to FIGS. 3b and 3c, each will carry a micro granule 48 (not shown in FIG. 4).

Figure 5:
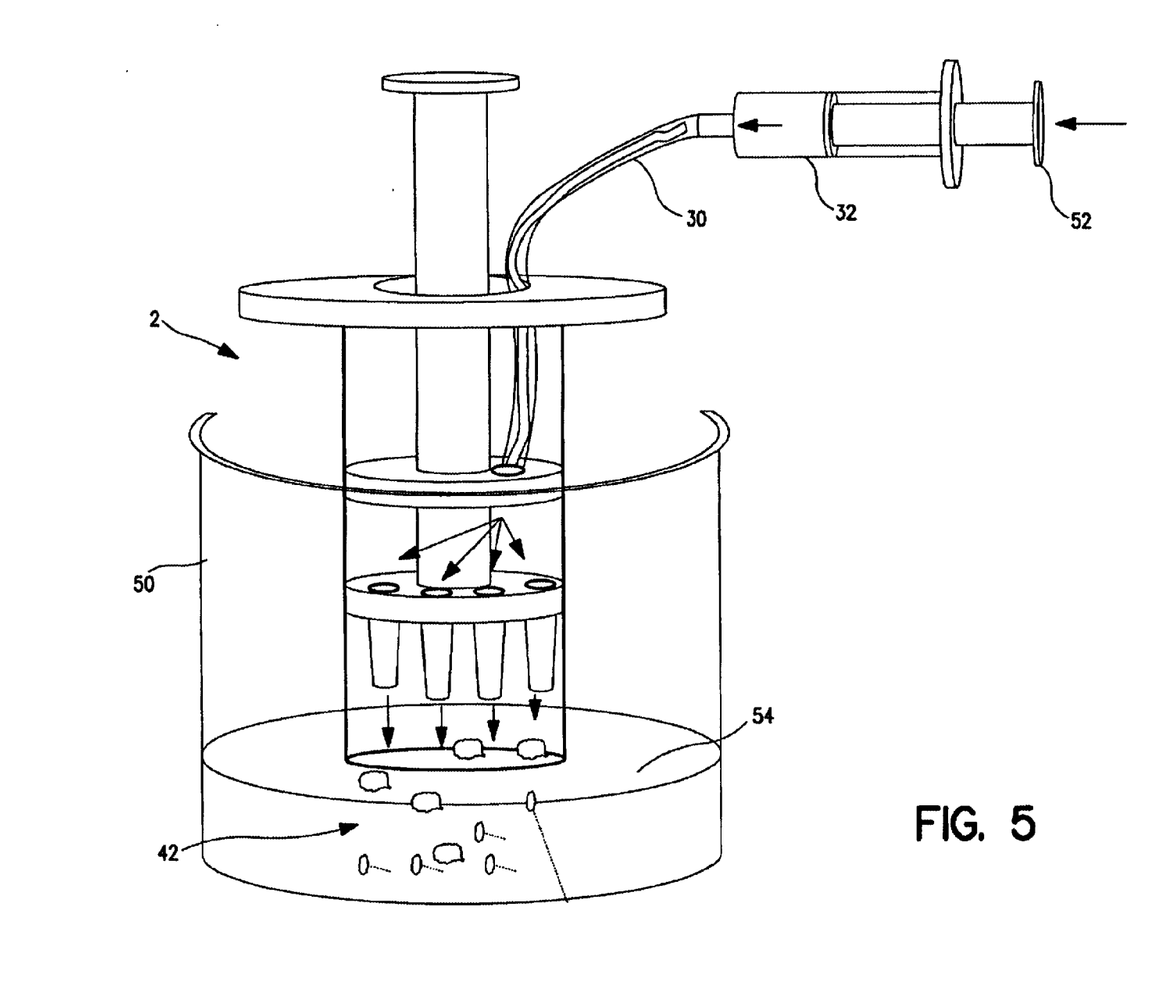
FIG. 5 is a perspective view of the myocyte micro granule retrieval device of FIG. 1, showing micro granules being transferred from the retrieval device to receptacle.

Turning now to FIG. 5, the retrieval device 2, having been removed from the donor area 34 and with each extraction probe 20 carrying a myocyte micro granule 42, is positioned over a receptacle 50, such as a beaker or the like. The myocyte micro granules 42 are then recovered from the extraction probes 20 by pumping air into the vacuum chamber 26. If the syringe 36 is attached to the tube 30, this can be done by depressing the syringe's plunger 52. Alternatively, air could be forced into tube 30 by an air pump or the like. Prior to or after deposit of the myocyte micro granules 42 into the receptacle 50, a quantity of a liquid medium 54, such as saline, can be added to act as a fluid carrier for subsequent delivery of the myocyte micro granules to an implantation site.

B. Myocyte Micro Granule Implantation

Figure 6:
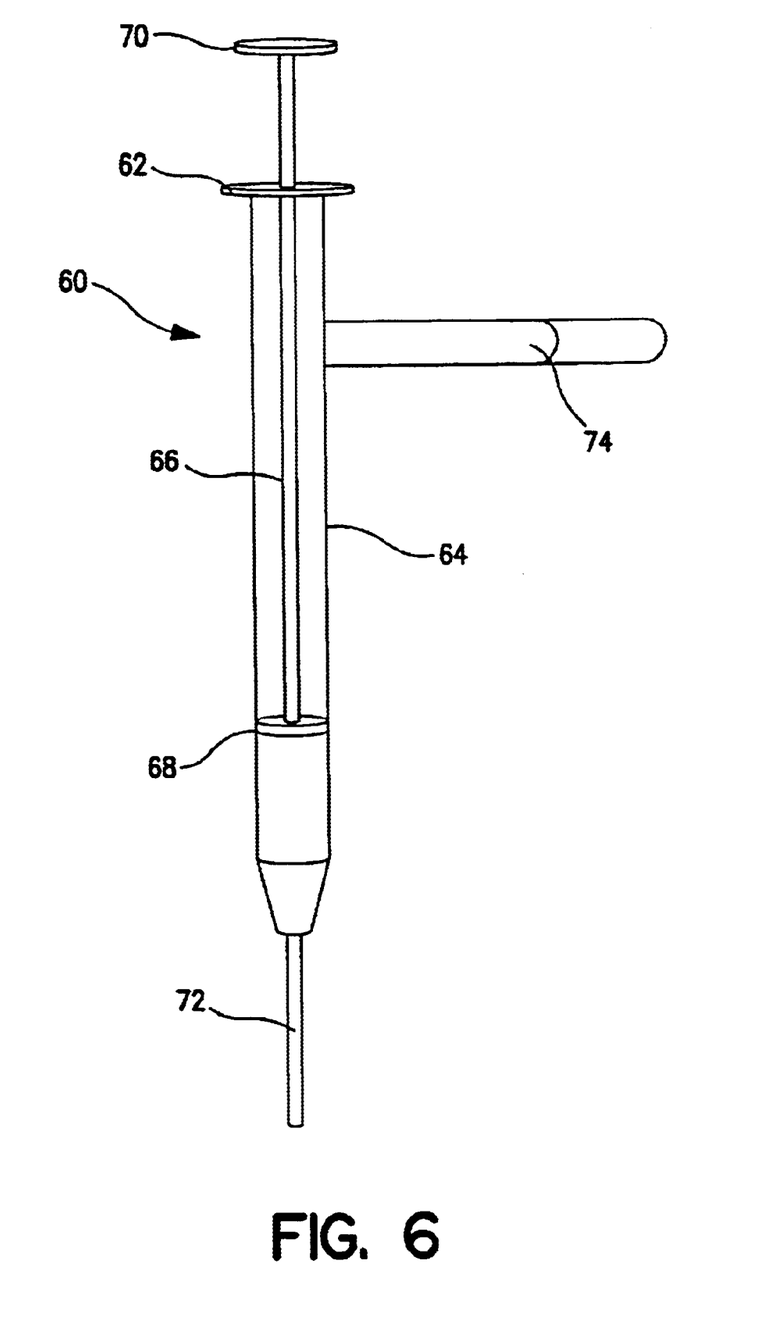
FIG. 6 is a side elevation view of a myocyte micro granule injection device that may be used for myocyte micro granule implantation, especially according to an epicardial approach.

Turning now to FIG. 6, an exemplary myocyte micro granule implantation device 60 is shown for use according to an epicardial approach. The implantation device 60 includes a syringe 62 having a hollow tubular body 64, a plunger 66 having a distal end 68 and a proximal end 70, and a hollow delivery needle 72. The implantation device 60 further includes an attached handle 74 for better gripping of the syringe 62 during implantation of the myocyte micro granules into a beating heart.

Figure 7:
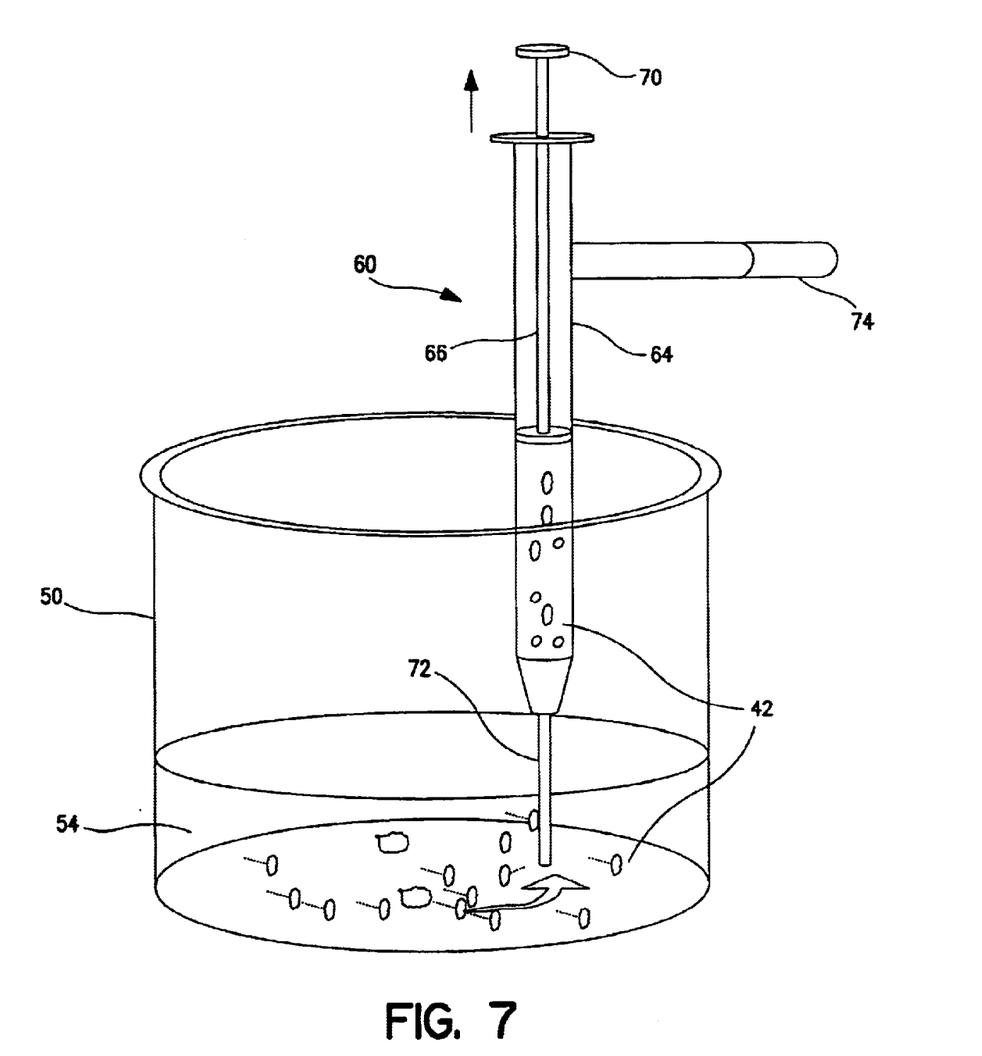
FIG. 7 is a perspective view of the myocyte micro granule injection device of FIG. 6, showing the injection device being filled with myocyte micro granules in a fluid carrier, readying it for use.
Figure 8:
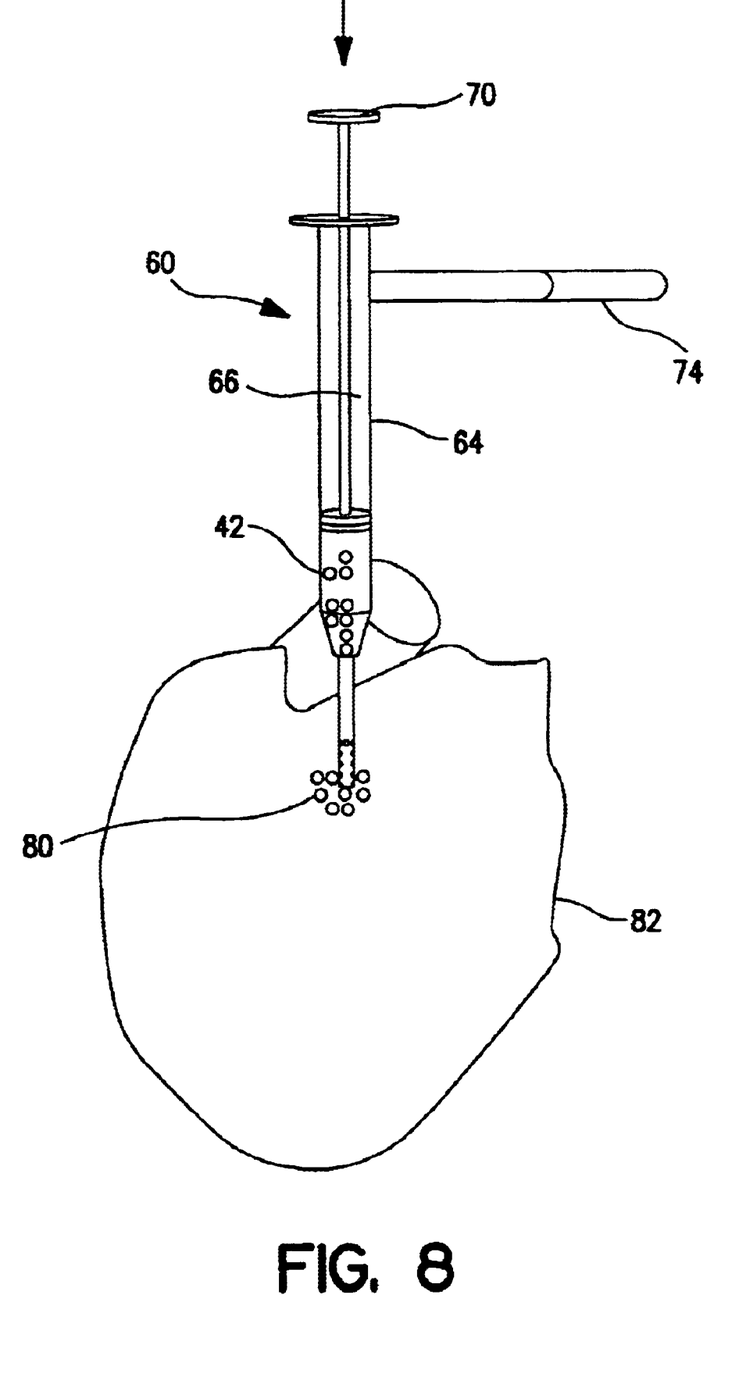
FIG. 8 is a diagrammatic perspective view of the injection device of FIG. 6, showing the implantation of myocyte micro granules into a myocardial wall according to an epicardial approach.

Turning now to FIG. 7, the implantation device 60 is shown inserted into the receptacle 50 containing the myocyte micro granules 42 disbursed in the liquid medium 54. The plunger 66 has been partially withdrawn from the tubular body 64, thereby drawing a portion of the material in the receptacle 50 into the implantation device 60. Then, as shown in FIG. 8, the implantation device 60 is positioned so that its delivery needle 72 enters an implantation area 80 of a patient's myocardium 82, such as an ischemic portion of the myocardial wall. The myocyte micro granules 42 are then injected into implantation area 60 and the implantation device 60 is withdrawn. If desired, several more injections may be performed until a desired quantity of myocyte micro granules are introduced into the implantation area.

Figure 9:
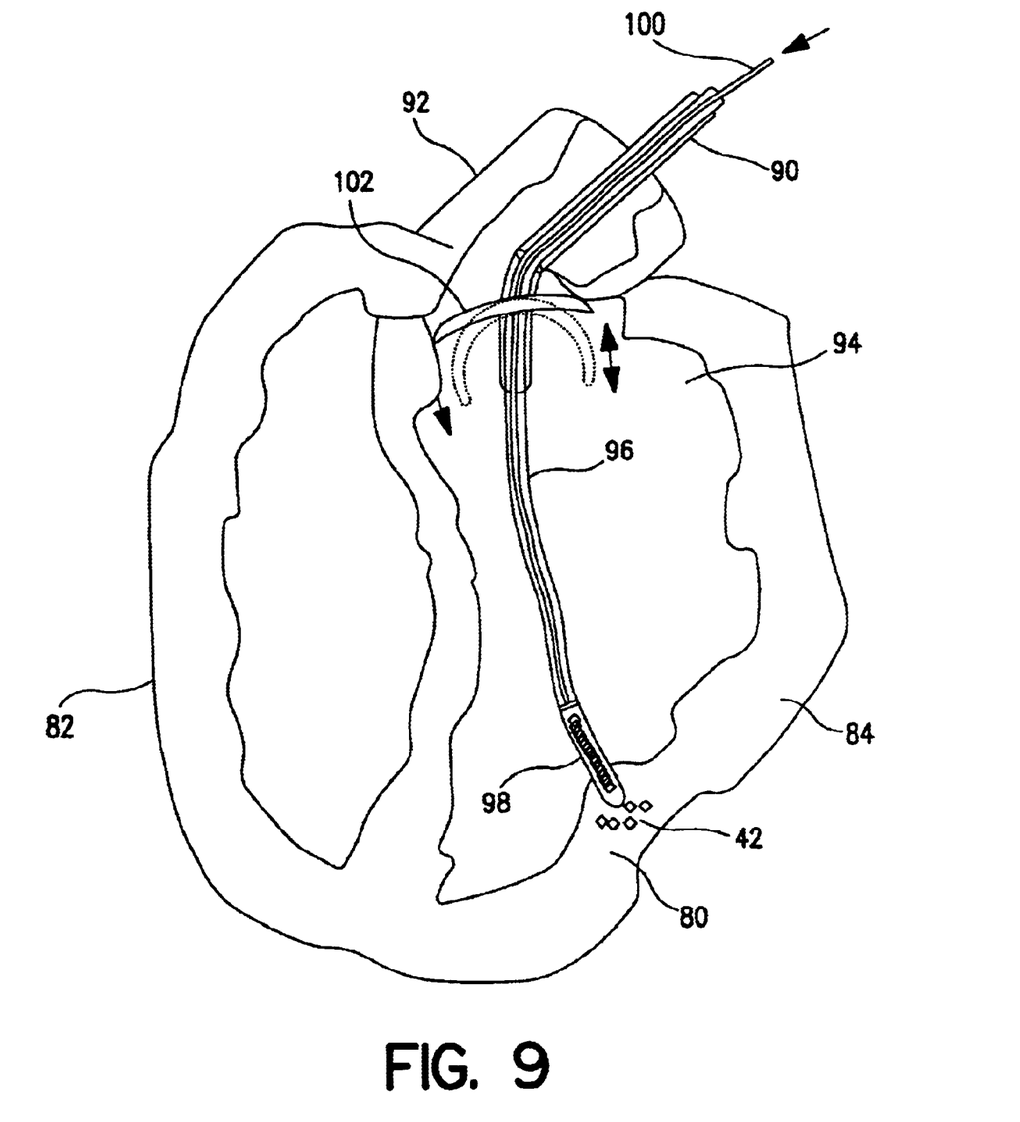
FIG. 9 is a diagrammatic perspective view of myocyte micro granule implantation using a transfemoral approach, and also showing a screen for blocking myocyte micro granule entry into the aorta.

Turning now to FIG. 9, the myocyte micro granules 42 are shown being injected into the implantation area 80 of a patient's myocardial wall 84 using a transfemoral approach. To that end, a catheter 90 is fed through the aorta 92 into the patient's left ventricle 94. Within the catheter 90 is an elongated flexible injection tube 96 having a sharpened hollow tip 98. An appropriate guidance system (not shown), such as a fiber optic probe, may likewise extend through the catheter 90 to assist in the catheter insertion process. With the catheter positioned in the left ventricle, the injection tube 96 is advanced until the hollow tip 98 enters the implantation area 80. Within the injection tube 96 is an elongated plunger 100. The plunger 100 is used to push the myocyte micro granules 42 from a femoral arterial entrance point (not shown) to the hollow tip 98. From there, the myocyte micro granules 42 are injected into the implantation area 80 via further extension of the plunger 100.

If desired, a retractable screen 102 can be mounted on or within the catheter 90. The screen 102 functions like an umbrella that can be opened and lodged at the exit point of the left ventricle 94, adjacent the aortic valve. During myocyte micro granule injection, the screen 102 allows blood to freely flow into the aorta, but has a mesh size which is selected to trap any myocyte micro granules that might spill from the implantation area 80 into the left ventricle 94. After micro granule injection is complete, the umbrella is closed in the manner shown by the double arrows in FIG. 9 to trap and hold any captured myocyte micro granules. Thereafter, the catheter 90 can be removed from the heart 82. Note that the retractable screen 102 may also be used when myocyte micro granules are injected via an epicardial approach. This would allow the screen 102 to catch myocyte micro granules in the event the medical practitioner inserts the implantation device 60 too far into the myocardial wall 84, such that the needle 72 actually passes through the other side and enters the left ventricle 94.

Accordingly, a method of autologous micro granule myocyte retrieval and implantation (AMMGRI) has been disclosed. While various embodiments of the invention have been described, it should be apparent that many variations and alternative embodiments could be implemented in accordance with the invention. It is understood, therefore, that the invention is not to be in any way limited except in accordance with the spirit of the appended claims and their equivalents.

What is claimed is:

1. A method for improving myocardial functionality in a patient having damaged myocardial tissue, comprising:
   locating a donor area of the patient containing healthy skeletal muscle;
   pretreating said donor area with an angiogenesis-promoting material;
   retrieving myocyte micro granules from said donor area;
   placing said myocyte micro granules in a fluid carrier;
   locating an implantation area of the patient's myocardium that contains damaged myocardial tissue; and
   without prior cell culturing, implanting said myocyte micro granules into said implantation area.

2. A method in accordance with claim 1 wherein said myocyte micro granules have a diameter of not more than 1 millimeter.

3. A method in accordance with claim 1 wherein said myocyte micro granules contain at least 100,000 myocyte cells.

4. A method in accordance with claim 1 wherein said myocyte micro granules contain at least 1,000,000 myocyte cells.

5. A method in accordance with claim 1 wherein said pretreating step includes either injecting said angiogenesis-promoting material in said donor area or introducing said angiogenesis-promoting material into a blood vessel supplying said donor area.

6. A method in accordance with claim 1 further including pretreating said donor area with one or more of a growth factor, transvected genes, enzymes, and cytokines.

7. A method in accordance with claim 1 wherein said myocyte micro granules are retrieved from said donor area using vacuum assistance.

8. A method in accordance with claim 1 wherein said myocyte micro granules are retrieved from said donor area using cutting.

9. A method in accordance with claim 1 wherein said implanting step is performed using either an epicardial approach or a transfemoral approach.

10. A method for improving myocardial functionality in a patient having damaged myocardial tissue, comprising:

locating a donor area of the patient containing healthy skeletal muscle;

pretreating said donor area with an angiogenesis-promoting material;

retrieving myocyte micro granules from said donor area;

placing said myocyte micro granules in a fluid carrier;

locating an implantation area of the patient's myocardium that contains damaged myocardial tissue; and without prior cell culturing, implanting said myocyte micro granules into said implantation area;

said myocyte micro granules being retrieved from said donor area using a myocyte micro granule retrieval device that includes:

one or more extraction probes;

distal tip(s) on said one or more extraction probes adapted to advance into a donor area of a patient containing skeletal muscle; and a retrieval system for causing said distal tip(s) to withdraw a myocyte micro granule upon removal thereof from said donor area.

11. A method in accordance with claim 10 wherein said myocyte micro granule retrieval device further includes:

a generally tubular body;

a plunger assembly slidably disposed in said body; and said one or more extraction probes being mounted to said plunger assembly.

12. A method in accordance with claim 11 further including a vacuum chamber formed on said plunger assembly.

13. A method in accordance with claim 12 wherein said vacuum chamber is defined by a pair of spaced disks mounted on said plunger assembly and slidably engaging said tubular body, said one or more extraction probes being mounted to a lower one of said disks and an upper one of said disks having an opening for introduction of a vacuum in said vacuum chamber.

14. A method in accordance with claim 11 wherein said myocyte micro granule retrieval device further includes an apertured plate mounted to a distal end of said tubular body to assist in presenting skeletal muscle at said donor area for myocyte micro granule retrieval.

15. A method in accordance with claim 10 wherein said retrieval system is a cutting system.

16. A method in accordance with claim 15 wherein said retrieval system includes a barb on said distal tip.

17. A method in accordance with claim 16 wherein said barb includes a trough for carrying said myocyte micro granules.

18. A method in accordance with claim 10 wherein said retrieval system is a vacuum assisted system.

19. A method in accordance with claim 18 wherein said vacuum assisted system includes:

said one or more extraction probes having a hollow bore extending to said distal tip(s); and a vacuum source in fluid communication with said hollow bore(s).

* * * * *